(12) United States Patent
Taylor et al.

(10) Patent No.: US 6,394,977 B1
(45) Date of Patent: May 28, 2002

(54) PRESSURE GAUGE WITH DIGITAL STEPPING MOTOR AND REUSABLE TRANSFER PLUG

(75) Inventors: Steven R. Taylor; Thomas D. Stout, both of Salt Lake City, UT (US)

(73) Assignee: Merit Medical Systems, Inc., Sandy, UT (US)

( * ) Notice: Subject to any disclaimer, the term of this patent is extended or adjusted under 35 U.S.C. 154(b) by 0 days.

(21) Appl. No.: 09/048,091

(22) Filed: Mar. 25, 1998

(51) Int. Cl.[7] .............................................. A61M 29/00
(52) U.S. Cl. .............................. 604/100.03; 604/100.01
(58) Field of Search ............................. 604/97, 96–100, 604/118, 121; 606/191, 192, 194; 128/DIG. 12, DIG. 13; 73/718, 724

(56) References Cited

U.S. PATENT DOCUMENTS

| | | | |
|---|---|---|---|
| 4,600,855 A | 7/1986 | Strachan ...................... 310/338 |
| 4,936,147 A | 6/1990 | EerNisse et al. ............... 73/702 |
| 5,009,662 A | 4/1991 | Wallace et al. .............. 606/192 |
| 5,135,488 A | 8/1992 | Foote et al. .................... 604/97 |
| 5,171,299 A | 12/1992 | Heitzmann et al. .......... 604/100 |
| 5,259,838 A | 11/1993 | Taylor et al. .................. 604/97 |
| 5,449,344 A | 9/1995 | Taylor et al. .................. 604/97 |
| 5,459,700 A | * 10/1995 | Jacobs ......................... 604/100 |
| 5,460,609 A | * 10/1995 | O'Donnell ................... 604/100 |
| 5,578,759 A | 11/1996 | Clayton ........................ 73/702 |

* cited by examiner

Primary Examiner—Sharon Kennedy
(74) Attorney, Agent, or Firm—Workman, Nydegger & Seeley (57) ABSTRACT

A pressure gauge for displaying the magnitude of fluid pressure generated within a syringe or another pressurized system. The pressure gauge is removably attachable to a syringe, and may be sterilized for reuse after each medical procedure. A piezoresistive transducer senses fluid pressure and generates an electrical signal that changes in response to changes in said fluid pressure. The electrical signal is converts d to digital signals by a microprocessor. A stepper motor responds to the digital signals to control a pointer that moves across a dial to display the magnitude of the fluid pressure. A small lithium battery that can withstand high temperatures supplies electrical power to the pressure gauge. A housing unit, comprising stainless steel and a transparent window, encases the components of the pressure gauge. After use, the pressure gauge is placed in an autoclave, thereby sterilizing the pressure gauge for reuse.

15 Claims, 3 Drawing Sheets

PRESSURE GAUGE WITH DIGITAL STEPPING MOTOR AND REUSABLE TRANSFER PLUG

BACKGROUND OF THE INVENTION

1. The Field of the Invention

The present invention relates to a pressure monitoring device for measuring the pressure that is generated during inflation of a balloon-tipped catheter and the duration of such inflation. More particularly, the present invention relates to a pressure monitoring device having a pressure transducer, a signal converter, and a display device that are substantially encased in a sterilizable housing for repeated use.

2. Relevant Technology

In recent years, balloon-tipped catheters have become increasingly useful in various medical procedures. For example, balloon-tipped catheters have been used to reduce the intrusiveness of medical procedures in various fields of medicine, such as urology, gynecology, cardiology, and the like. Particularly in the treatment of coronary artery disease, the use of balloon-tipped catheters and their associated fluid pressurization systems has become widespread.

Coronary artery disease is the narrowing of the arteries that feed oxygen-rich blood to the heart. The heart needs adequate amounts of oxygen to continually and efficiently pump blood throughout the body. When arteries leading to the heart become narrowed and constricted due to coronary artery disease, several problems can develop. A person with coronary artery disease can experience angina, which is characterized by chest pain or pressure that radiates to the arm or jaw and is caused by a lack of oxygen-rich blood to the heart muscle. If untreated, coronary artery disease can lead to or contribute to heart failure and death.

In recent years, coronary angioplasty has become a common and accepted alternative to the vastly more intrusive coronary bypass surgery. Coronary bypass surgery involves surgical access to the heart, placing the patient on an extracorporeal blood oxygenation system so that the heart can be stopped for surgery, and then surgically attaching one or more passageways by which blood can bypass a clogged coronary artery, all under general anesthesia. Coronary angioplasty, which can be performed using a local anesthetic, involves running a dilation catheter (a catheter having an inflatable balloon near the end) to the diseased artery and then inflating the balloon in order to compress plaque within the artery, thereby obtaining increased blood flow to the heart. Compared to coronary bypass surgery, coronary angioplasty is less intrusive and traumatic, typically involves less risk to the patient, and significantly reduces the patient's discomfort and recovery time.

During inflation of the balloon during angioplasty, no blood can flow through the artery that is being mechanically dilated. The disruption of blood flow must be limited in duration to about 20 to 60 seconds, so as to avoid tissue damage due to oxygen deprivation. Hence, it is important to carefully monitor the inflation pressure and duration to ensure that blood flow is restored before tissue damage can occur. In most cases, it is not possible to adequately dilate a diseased artery in a single inflation. In cases where it is necessary to undertake multiple inflations in the same artery, it is important to allow sufficient time between successive inflations so that the tissues fed by the diseased artery can become fully oxygenated before blood flow is disrupted again. At the same time, a successful angioplasty procedure requires that the dilation of the artery be conducted for a significant period of time.

In addition to monitoring in real time the inflation pressure and duration, it is also important for the physician performing the angioplasty to have access to historical information regarding the duration and intensity of past inflations and deflations. Accordingly, various devices and gauges have been developed for monitoring inflation and deflation of balloon tipped catheters during angioplasty. All pressure gauges for measuring pressure within a syringe generally have at least two primary components: a pressure sensing unit and a display unit. The pressure sensing unit is positioned to be in fluid communication with the syringe often by being mounted directly thereon. The display unit typically comprises a dial, a liquid crystal display, a graphical device, or another visible system that displays the magnitude of the fluid pressure that is detected by the pressure sensing unit. The pressure sensing unit is connected with the display unit electrically, mechanically, or by other means by which information may be transmitted.

One common pressure gauge is configured with the pressure sensing unit positioned on the syringe, while the display unit is located perhaps several feet away from the syringe. Typically, electrical cables connect the pressure sensing unit with the display unit. It has been found that use of such pressure gauges can be somewhat awkward, since the physician who operates the syringe must repeatedly alternate his or her attention from the syringe to a the display unit or must receive inflation information second-hand from an assistant who monitors the display unit. In addition, the cables and relatively bulky display unit may cause the operating area to become cluttered.

The problems associated with physical separation of the display unit and the pressure sensing unit have been addressed by using integrated pressure gauges in which the pressure sensing unit and the display unit are combined in a self-contained device. Such integrated gauges are generally attached directly to the syringe. Accordingly, an integrated gauge may be more convenient to use, because the operating physician can more exclusively concentrate on the syringe area during the medical procedure. Because integrated gauges are positioned on the syringe in communication with the catheter fluid and relatively near the patient, such gauges must be sterilized for reuse or disposed after the medical procedure. In practice, disposable gauges are often prohibitively expensive, and sterilizable gauges are therefore generally preferred.

Liquid crystal displays (LCD's) and other mechanisms conventionally used for displaying information measured by digital systems cannot withstand the high temperatures used during sterilization procedures. In addition, a self-contained power supply has not been available in the past that can suitably be used in an integrated pressure gauge and that can withstand sterilization temperatures. While light-emitting diodes (LED's) would generally be able to withstand sterilization temperatures, their use in a self-contained pressure gauge would be undesirable due to their high energy requirements, which would quickly deplete self-contained energy supplies. Thus, due to the impracticability of using commercially available display devices that can be used with digital pressure gauges, conventional sterilizable integrated pressure gauges have been exclusively analog and mechanical since analog displays consume little or no energy and have no parts that are destroyed by heat sterilization processes.

Integrated mechanical pressure gauges have a sensor diaphragm that may be placed in fluid communication with the syringe, so as to be physically displaced in response to generated fluid pressure. The distance of displacement of the diaphragm is typically proportional to the magnitude of the fluid pressure. The diaphragm may be mechanically connected to a C-shaped flexible metal member, such as a brass or bourdon tube, that is used to mechanically convert the linear displacement of the diaphragm into rotational displacement of a spindle and a pointer across a graduated numerical dial. In this manner, the dial mechanically displays the magnitude of the fluid pressure within the syringe. The integrated pressure gauge is generally removably attached to the syringe such that the gauge may be placed in an autoclave or otherwise sterilized for reuse after each medical procedure.

Sterilizable integrated mechanical pressure gauges of the prior art have experienced a number of problems, however. For instance, the many moving parts within mechanical gauges are relatively delicate and can be easily damaged by mishandling or misuse. For example, if a mechanical pressure gauge is dropped, it can easily be thrown out of calibration by gear teeth being jarred out of alignment or by any of a number of moving parts being broken, dislodged, or bent. In addition, the bourdon tube can be easily damaged and is also subject to fatigue after repeated use. When a bourdon tube experiences fatigue, the pressure gauge in which it is used gives faulty and unreliable readings. Furthermore, mechanical pressure gauges cannot be systematically calibrated to compensate for temperature effects, which can consequently cause inconsistent pressure measurements due to fluctuations in temperature.

Mechanical pressure gauges may also be thrown out of calibration for any of a number of reasons. It is often difficult to reliably or systematically calibrate such mechanical gauges to respond to the effects of prolonged use or simply to ensure that the gauges are "zeroed" prior to each use. Furthermore, unlike digital pressure gauges, conventional integrated mechanical pressure gauges lack the means for recording and retrieving data relating to past inflation pressures and the duration of past inflations which are generally desirable when performing angioplasty.

In view of the foregoing, it is apparent that it would be an advancement in the art to provide pressure gauges that are less vulnerable to damage from mishandling or misuse than existing integrated, sterilizable gauges.

It would be a further advancement in the art to provide pressure gauges that measure pressure without using a bourdon tube or similar flexible metal member for providing a mechanically driven pressure reading in response to fluid pressure.

It would be another advancement in the art to provide pressure gauges that could be calibrated so as to compensate for temperature affects and to generate reliable measurement readings throughout a range of temperatures.

It would be an advancement in the art to provide integrated and self-contained pressure gauges that utilize an electronic pressure measurement system yet may be removably attached to a syringe and easily and repeatedly sterilized for reuse.

It would be still another advancement in the art to provide integrated and sterilizable pressure gauges which are capable of storing data that relates to past inflation pressures and the duration of past inflations for later retrieval.

It would be another advancement in the art to provide integrated and sterilizable pressure gauges which may be initialized prior to each use to ensure that the gauge is correctly calibrated and will give an accurate and reliable reading.

Such pressure gauges are disclosed and claimed herein.

SUMMARY OF THE INVENTION

The present invention relates to pressure gauges for measuring the pressure generated within a balloon-catheter system or in other pressure-generating systems. The pressure gauges of the invention utilize an analog-to-digital-to-analog method of sensing and displaying the generated fluid pressure. Moreover, the magnitude of the fluid pressure is preferably displayed in a mechanical fashion, thereby eliminating the need for liquid crystal displays and light emitting diodes of the prior art.

When the pressure gauges of the invention are used in balloon-catheter systems or other medical applications, they are preferably capable of being sterilized for reuse. Sterilization of the pressure gauge may be facilitated by encapsulating the pressure sensing components within a sterilizable housing, typically comprising stainless steel, and by providing pressure sensing components that are able to withstand elevated sterilization temperatures. Sterilization is conducted, for example, after the pressure gauge has been used with a balloon-tipped catheter in a medical procedure. The pressure gauge is removed from the syringe and is subjected to suitable sterilization procedures, which may include sterilization by thermal means in an autoclave and/or by chemical means.

The pressure gauge includes a transducer, which is preferably a piezoresistive semiconductor transducer, for sensing the fluid pressure that is generated within the syringe. The transducer preferably has a sterilizable diaphragm that is adapted to be in fluid communication with the syringe when the pressure gauge is attached to the syringe. The transducer generates an electrical current that is a function of the magnitude of the generated fluid pressure.

The analog-to-digital function of the pressure gauges is preferably performed by a microprocessor, which converts the electrical current to a series of digital signals. The subsequent digital-to-analog function of the pressure gauges occurs as the digital signals are directed to an analog or mechanical display device, which preferably includes a miniaturized stepper motor. The stepper motor responds to the digital signals by causing a specified angular displacement of a spindle and a pointer across a graduated numerical dial so as to display the magnitude of the generated fluid pressure.

The pressure gauges of the present invention eliminate many of the mechanical or moving components of existing pressure gauges that are sensitive to mishandling or misuse. As a result, the pressure gauges of the invention are less likely to be damaged than prior art devices. In addition, the components of the pressure gauges of the invention are not subject to fatigue during repeated use because there is no bourdon tube or other similar flexible metal member.

Because the pressure gauges disclosed herein include a microprocessor that generates digital signals in response to the fluid pressure in the syringe, the pressure gauge may be adjusted to compensate for temperature effects. The pressure gauge may also be initialized, or "zeroed", at the beginning of each use in order to calibrate the system and to provide reliable and accurate measurement readings. The microprocessor may also store in its memory a history of the magnitude and duration of the generated fluid pressure, which is made available for later retrieval. Such pressure history may be retrieved, for example, by causing the pointer on the pressure gauge to indicate past inflation measurements on the dial. Alternatively, pressure history may be displayed by using an infrared emitter exposed on the surface of the sterilizable housing and a corresponding remote receiver unit that displays the past inflation measurements.

The pressure gauges preferably combine several high temperature-resistant components such that the resulting electronic system may withstand the extreme temperatures needed for sterilization, particularly when medical procedures are to be monitored with the pressure gauges. For example, a high temperature-resistant battery is preferably used to generate electrical power for the pressure gauge. In addition, the use of a stepper motor to display the magnitude of the generated fluid pressure on a numerical dial eliminates the need for conventional digital displays that would be damaged during sterilization, such as those that involve liquid crystals. The stepper motor further provides advantages, in that it requires relatively little energy, thereby extending the useful life of the battery and, as a result, the entire pressure gauge.

In view of the foregoing, it is an object and feature of the present invention to provide pressure gauges that are less vulnerable to damage from mishandling or misuse than existing integrated, sterilizable gauges.

It is a further object and feature of the present invention to provide pressure gauges that measure pressure without using a bourdon tube or similar flexible member for providing a mechanically driven pressure reading in response to fluid pressure.

It is another object and feature of the present invention to provide pressure gauges that could be calibrated so as to compensate for temperature effects and to generate reliable measurement readings throughout a range of temperatures.

It is another object and feature of the present invention to provide integrated and self-contained pressure gauges that utilize an electronic pressure measurement system yet may be removably attached to a syringe and easily and repeatedly sterilized for reuse.

It is still another object and feature of the present invention to provide integrated and sterilizable pressure gauges which are capable of storing data that relates to past inflation pressures and the duration of past inflations for later retrieval.

It is another object and feature of the present invention to provide integrated and sterilizable pressure gauges which may be initialized prior to each use to ensure that the gauge is correctly calibrated and will give an accurate and reliable reading.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to pressure gauges for measuring the pressure generated within a syringe of a balloon-catheter system or in other pressure-generating systems. The pressure gauges of the invention utilize an analog-to-digital method of sensing and displaying the generated fluid pressure. Moreover, the magnitude of the fluid pressure is preferably displayed in a mechanical fashion, thereby eliminating the need for liquid crystal displays or light emitting diodes of the prior art.

As disclosed herein, the pressure gauges are described primarily for use with a balloon-catheter system or other medical applications. However, the invention extends to other pressure gauges that function according to the principles disclosed herein. For example, pressure gauges incorporating the analog-to-digital measurement system of the invention are contemplated by the invention, whether they are use(in medical, industrial, or other applications. Pressure gauges for use in medical procedures are described in detail herein because such gauges generally require sterilizability and high temperature resistance, which may or may not be required in industrial or other settings.

When the pressure gauges are intended to be used for monitoring the inflation of a balloon-tipped catheter system or in other medical procedures, the pressure gauges are preferably sterilizable, self-contained units. Sterilizable pressure gauges preferably include a stainless steel or a similar sterilizable housing that encases as many as all of the other components of the pressure gauge.

The sterilizable housing is removably attached to the syringe or another hydraulic portion of the balloon-tipped catheter system. After the end of each medical procedure that uses the pressure gauge, the sterilizable housing is removed from the syringe and is sterilized for reuse. The sterilization process may involve thermal sterilization in an autoclave or a sterilizing chemistry that may include, for example, gluteraldehydes or ethylene oxide. If thermal sterilization is used, the components of the pressure gauge that are contained by the housing should be resistant to sterilization temperatures.

The pressure gauges use a transducer, which is preferably a piezoresistive semiconductor transducer, to measure the fluid pressure generated within a syringe or another chamber. The transducer is positioned in fluid communication with the pressurized fluid. Electrical signals generated by the transducer are transmitted to an analog-to-digital convertor, preferably a microprocessor, which converts the electrical signal into a series of digital signals. The digital signals cause a display device to generate a visual representation of the magnitude of the fluid pressure.

The present invention includes the novel pressure gauges that are disclosed herein. In addition, the invention extends to these pressure gauges in combination with a balloon-tipped catheter system or any other system in which a fluid pressure is generated and measured. Methods of using the pressure gauges to monitor fluid pressure within a catheter system are also disclosed.

The term "sterilizable," as used in the specification and the appended claims, shall indicate that object or a component that is so characterized is capable of being sterilized to the degree customarily required in medical applications. The term is intended to mean that an object or component may be placed in a condition to be reused in the medical procedure for which it is designed, substantially without risk of causing a patient to be exposed to pathogenic contaminants. A "sterilizable" object or component may be sterilized with one or more of a number of processes, including, but not limited to, thermal and chemical sterilization.

The term "mechanical", as used in the specification and the appended claims, when used to describe a pressure gauge or components thereof, shall have its ordinarily understood meaning. For example, a completely "mechanical" pressure gauge operates in response to the interaction of physically connected moving parts that are powered by mechanical sources of energy, such as potential energy stored in a pressurized gas. Likewise, in a "mechanical" or "mechanically produced" visual display, information is displayed and represented according to the physical position of at least one moving part.

The term "fluid communication" as used herein is intended to mean that two objects or components are positioned relative to one another such that a fluid pressure is pneumatically or hydraulically transmitted between and experienced by each of the two objects. The transmission of fluid pressure may be direct or indirect. An example of "fluid communication" is seen between the diaphragm of a piezoresistive semiconductor transducer and a syringe when the diaphragm is placed in contact with fluid contained within the syringe.

Figure 1:
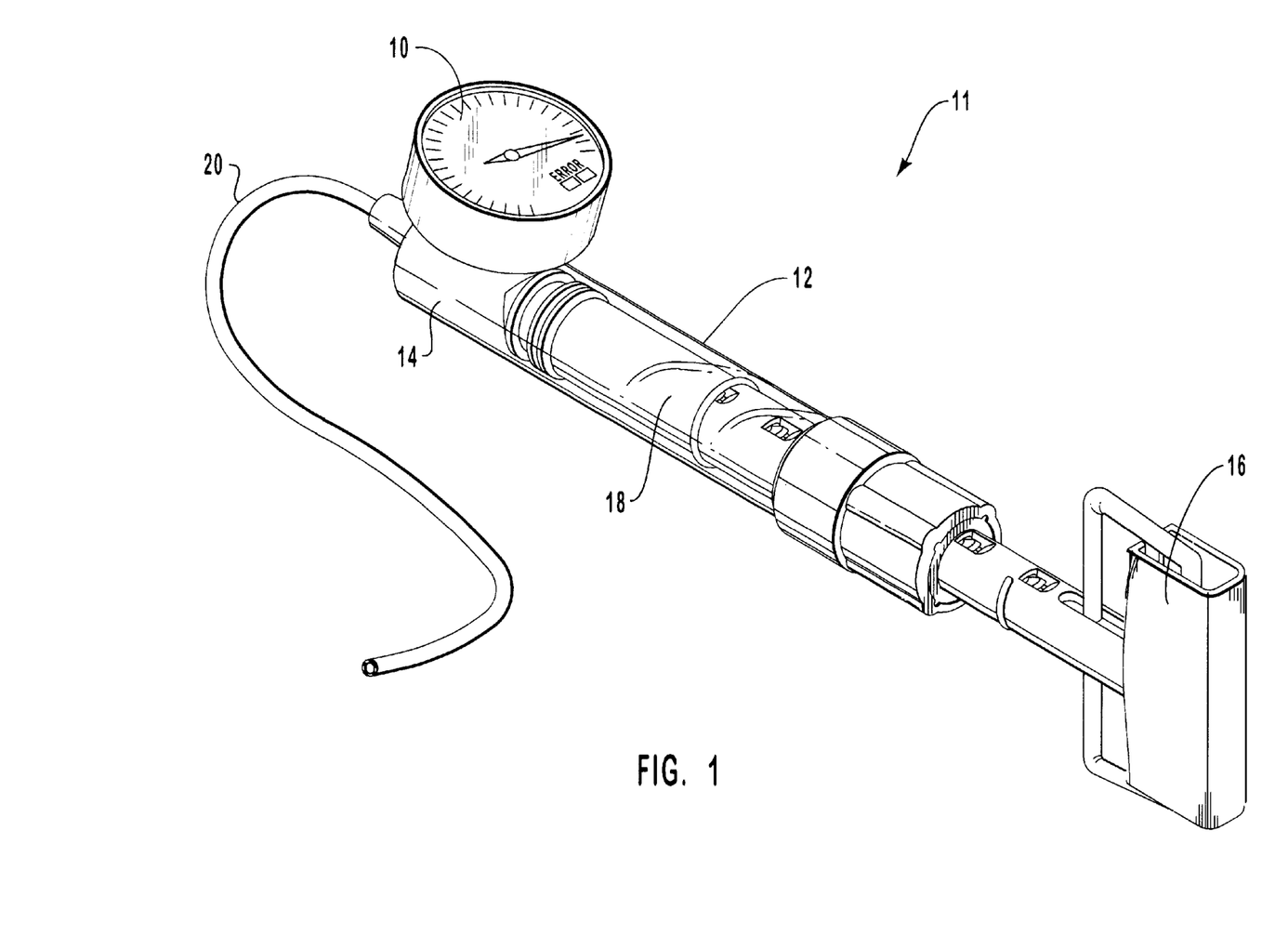
FIG. 1 is a perspective view of a pressure gauge of the present invention removably attached to a syringe of a balloon-catheter system.

The invention may be best understood by referring to FIGS. 1–5, which illustrate the elements, features, and operation of various embodiments thereof. Reference is first made to FIG. 1, which illustrates one presently preferred embodiment of a syringe apparatus assembled in accordance with the present invention. The syringe apparatus 11 of FIG. 1 includes a pressure gauge, shown generally at 10 and a syringe assembly shown generally at 12. Pressure gauge 10 visually displays a magnitude of fluid pressure that is generated by syringe assembly 12 and is removably attached to a hollow barrel 14 of syringe assembly 12. Syringe assembly 12 includes a plunger 18 slidably disposed within barrel 14, and a handle 16 connected to an end of plunger 18 extending out of barrel 14. As a physician manipulates handle 16, plunger 18 is forced into barrel 14, thereby expelling fluid from barrel 14 through pressure tubing 20. During procedures involving a balloon-tipped catheter, pressure tubing 20 is connected to the input end of such a catheter so that fluid expelled from barrel 14 will inflate the balloon of the balloon-tipped catheter. It will be understood that syringe assembly 12 is one example of syringe means for generating a fluid pressure that is sufficient to inflate a balloon-tipped catheter.

The syringe assembly 12 illustrated in FIG. 1 is more particularly described in U.S. Pat. Nos. 5,449,344 to Taylor et al. and 5,135,488 to Foote et al., which are incorporated herein by reference for purposes of disclosure. However, it is to be understood that the nature and mechanical aspects of syringe assembly 12 are not limited to those specific features illustrated in FIG. 1 or disclosed in the foregoing patents, and that a variety of different types of syringe designs could be utilized without departing from the spirit and scope of the present invention. Indeed, the pressure gauges disclosed herein may be adapted to measure fluid pressures generated within devices other than syringes. In these cases, the pressure gauge is adapted to be in fluid communication with a chamber or another fluid system in which a fluid pressure may be generated.

Figure 2:
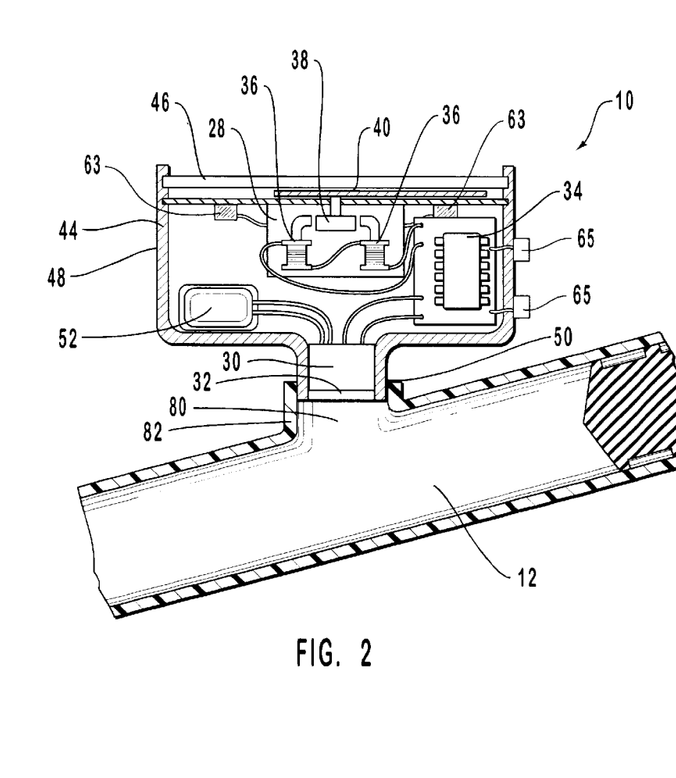
FIG. 2 is a cross-sectional view of the pressure gauge that reveals the components and elements of the pressure gauge that are encased within a housing.

As illustrated in the cross-sectional view of FIG. 2, pressure gauge 10 is an example of pressure monitoring means for sensing fluid pressure and for producing a visual display of the magnitude of the fluid pressure. In order to perform the foregoing functions, pressure gauge 10 includes transducer means for sensing fluid pressure and for outputting an electrical signal that changes in response to changes in the fluid pressure. The term "fluid pressure" as used herein is intended to apply to either a hydraulically or pneumatically-applied pressure within a system. Generally, fluid pressure is measured as a departure from a baseline pressure, which may be atmospheric pressure.

A typical transducer for detecting the pressure within a fluid system includes a diaphragm than mechanically deflects in response to fluid pressure. This deflection causes corresponding strain within elements of a Wheatstone bridge in order to produce a variable electrical current that changes in response to changes in the fluid pressure. Typically, the variable current is substantially proportional to the fluid pressure, but other functions of the fluid pressure may be used and would certainly be encompassed by the present invention. Transducers for generating an electrical current that is a function of fluid pressure are wellknown in the art.

One example of transducer means according to the invention is illustrated in FIG. 2 as a piezoresistive semiconductor transducer 30. Transducer 30 preferably has a sterilizable diaphragm surface 32 positioned so as to be in fluid communication with syringe 12 when pressure gauge 10 is positioned thereon. Diaphragm surface 32 is preferably stainless steel, but may be another suitable material which is capable of being sterilized for reuse in medical procedures. A preferred piezoresistive semiconductor transducer that has a sterilizable diaphragm surface is available from Sentir Semiconductor, Inc. of Santa Clara, Calif., model number 550-0012-ABOO. flowever, when pressure gauge 10 is intended to be used in industrial settings or in other situations that do not require sterile conditions, diaphragm surface 32 does not need to be sterilizable.

While a piezoresistive semiconductor transducer is preferred, the transducer means could instead include another device, such as a conventional strain gauge which has been known and used in the art for may kinds of pressure monitoring applications, or a fiber optic transducer. However, when the transducer is used with a balloon-catheter apparatus, as depicted in FIGS. 1 and 2, any such transducer should be capable of withstanding the high temperatures or other conditions that are experienced during sterilization.

Pressure gauge 10 further includes conversion means for receiving electrical signals from the transducer and for converting the electrical signals into a series of digital signals. For example, such conversion means may be a microprocessor 34 that functions as an analog-to-digital converter. In particular, microprocessor 34 preferably has electronic circuitry designed for converting the analog electrical signal generated by transducer 30 to a digital form. While it should be understood that a variety of microprocessors can function suitably well in pressure gauge 10, a presently preferred microprocessor 34 is available as model number PIC 14000 from Microchip, Inc. of Chandler, Ariz.

Display means for receiving the digital signals and for mechanically producing a visual display of the magnitude of the generated fluid pressure are also included in pressure gauge 10. Such display means may include, for example, a stepper motor 28 that can incrementally adjust a pointer so as to accurately display the magnitude of the measured fluid pressure. The stepping motor may include a pair of solenoid devices 36 that are electrically connected to the conversion means. The solenoid devices 36 are consecutively actuated in response to the digital signals, thereby causing rotation of a spindle through an angle that is determined by the magnitude of the fluid pressure. The stepping motor may be any of a number of conventional miniaturized stepping motors that are typically used in watch making. For example, the M-S 310 series of miniaturized stepper motors available from Switech, a division of S.A. Fabriques d'Ebauches of Switzerland, may be advantageously used in pressure gauges of the present invention. Some miniaturized stepper motors are capable of rotating a spindle in increments as small as ⅓ degree, although larger angular increments may certainly be acceptable in many embodiments according to the invention.

Figure 3:
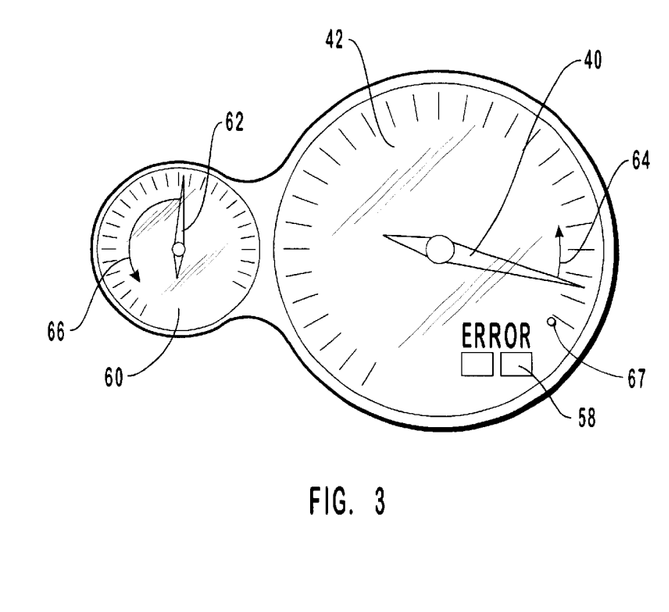
FIG. 3 is a top view of a graduated numerical dial of the pressure gauge for displaying the magnitude of a measured fluid pressure.

The solenoid devices 36 of stepper motor 28 operate to rotate spindle 38, which in turn causes movement of pointer 40. As seen in FIG. 3, a preferred display system includes pointer 40 that rotates in relation to a numerically graduated dial 42. The foregoing combination of a stepper motor and a numerical dial allows the pressure gauge 10 to digitally process and mechanically display pressure data without using liquid crystal displays or other visual display mechanisms that cannot withstand sterilization temperatures without using light emitting diode displays that cause relatively large amounts of power and without using delicate mechanical components that could be easily damaged.

FIG. 2 further illustrates housing means for substantially encasing the conversion means and the display means. The housing means preferably include a stainless steel bottom housing 44 and a transparent window 46 through which the display means may be viewed. As seen in FIG. 2, bottom housing 44 and window 46 may encase as many as all other components of pressure gauge 10 with the exception of diaphragm surface 32 of transducer 30, which remains exposed to the environment. The stainless steel surface 48 of bottom housing 44 and the glass or crystal of transparent window 46 are readily sterilized when pressure gauge 10 is placed within an autoclave or exposed to a sterilizing chemistry. The housing means advantageously avoids surface irregularities to the extent possible in order to provide a generally even surface that may be relatively easily sterilized. Avoiding surface irregularities preferably includes ensuring that diaphragm surface 32 of transducer 30 is generally flush with the adjacent portions of bottom housing 44. When the pressure gauge is used in settings where sterile conditions are not critical, the housing system does not need to be sterilizable, but preferably at least protects the internal components from environmental conditions as needed.

Pressure gauge 10 preferably has attachment means for removably positioning pressure gauge in fluid communication with a syringe barrel or another chamber in which fluid pressure is generated. One example of attachment means includes a neck portion 50 or other male component on pressure gauge 10 that mates with a corresponding port 80 or other female component in the syringe assembly such that diaphragm surface 32 is exposed to fluid pressure. Forming a male component such as neck portion 50 within bottom housing 44 of pressure gauge 10 provides somewhat improved access to the surfaces of pressure gauge 10 for sterilization purposes compared to the use of a female component on pressure gauge 10. However, optionally, the attachment means can comprise a female component on pressure gauge 10 and a corresponding male component on the syringe apparatus while still maintaining the ability of pressure gauge 10 to be sterilized. The attachment means may further include a disposable O-ring that is used to seal the interface between syringe barrel 14 and pressure gauge 10.

The syringe barrel 14 may include a housing well 82 attached or integrally formed on the outer surface of barrel 14 in order to support neck portion 50 of bottom housing 44. Pressure gauge 10 may be snap fitted, threadedly mated, or attached to a syringe apparatus in a fluid-tight fashion by any of a number of other suitable means that may be known in the art. Instead of mounting pressure gauge 10 directly on syringe barrel 14, the attachment means may comprise a disposable or sterilizable fitting, a segment of pressure tubing, or the like that extends from the syringe barrel 14 to transducer 30. It is often preferable to provide attachment means such that pressure gauge 10 is oriented at an angle with respect to the radius of syringe barrel 14 that facilitates viewing of the display means by a physician during operation of the syringe.

It should be understood that in some applications, particularly where sterile conditions are not critical, the pressure gauge may be permanently mounted to a system that generates fluid pressure.

The pressure gauges of the invention may be equipped with one or more buttons 65 that allow the user of the pressure gauge to select one or more specified functions. For example, actuation of a button 65 may send a signal to microprocessor 34, thereby causing a selected operation to be executed. Examples of uses of buttons 65 are disclosed in greater detail herein.

Figure 4:
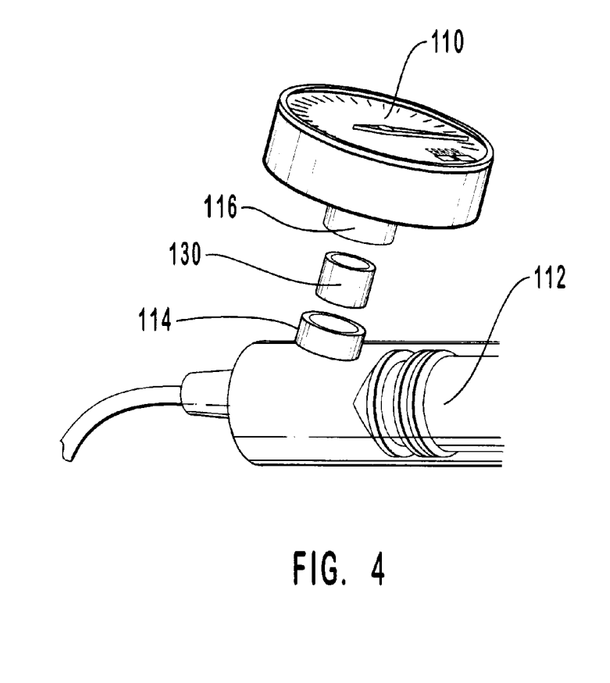
FIG. 4 is an exploded perspective view of a syringe and an embodiment of a pressure gauge according to the invention, in which a pressure transducer is removable from the display unit.

FIG. 4 depicts an alternative embodiment of a pressure gauge in which a piezoresistive semiconductor transducer 130 is removable from the remainder of pressure gauge 110. In order to removably attach pressure gauge 110 to syringe assembly 112, pressure transducer 130 is inserted or otherwise disposed into both an orifice 114 on syringe assembly 112 and a socket 116 on pressure gauge 110. After use, pressure transducer 130 may be discarded or may be sterilized for reuse. In other respects, the elements, features, and operation of pressure gauge 110 may be similar to those of pressure gauge 10 of FIGS. 1 and 2.

Pressure gauge 10 of FIGS. 1 and 2 and the other pressure gauges disclosed herein also include power generation means for providing sufficient electrical power such that the pressure gauge senses the fluid pressure and visually displays the magnitude thereof. The power generation means typically provides electrical power to at least transducer 30, microprocessor 34 and stepper motor 28. Preferably, the power generation means includes a battery 52 that is small enough to be encased in the housing means. When the power generation means is contained within the housing means and thermal sterilization is to be used, the power generation means may be any suitable battery or other power supply apparatus that is capable of sterilization temperatures, which are typically at least 135° C. One presently preferred example of power generation means is a miniaturized, high temperature resistant lithium battery such as battery model numbers BR1225A and BR1632A, which are manufactured by Matsushita Battery Industry Co., Ltd., of Osaka, Japan.

Alternatively, the power generation means may be external to the housing means and connected to pressure gauge 10, for example, by electrical leads provided on the surface of bottom housing 44.

There are several available methods by which the pressure gauges of the invention may be turned on or otherwise activated for use. According to a preferred method, the pressure gauge is continually activated such that pressure transducer 30 is repeatedly monitored at regular intervals to determine whether the pressure sensed thereby has changed since the last interval. The regular interval at which the pressure transducer is monitored may be selected from any suitable time period, one example of which is about 1 second. If a change in sensed pressure is detected, thereby indicating that the pressure gauge is in use, microprocessor 34 enters or remains in an active state. In this active state, the pressure gauge is in condition to monitor fluid pressure in an ongoing manner.

If no change in sensed pressure is detected for an extended period, thereby indicating that the pressure gauge is not in use, microprocessor 34 enters or remains in a dormant state. In this dormant state, little or no activity is conducted other than repeatedly monitoring the pressure transducer at regular intervals. The dormant state conserves the energy stored in the power supply while eliminating the need for "turning off" the pressure gauge as understood in the traditional sense. Alternatively, the foregoing system of active and dormant states may be replaced by a system whereby button 65 or another actuating mechanism allows a user to manually turn the pressure gauge on and off.

Figure 5:
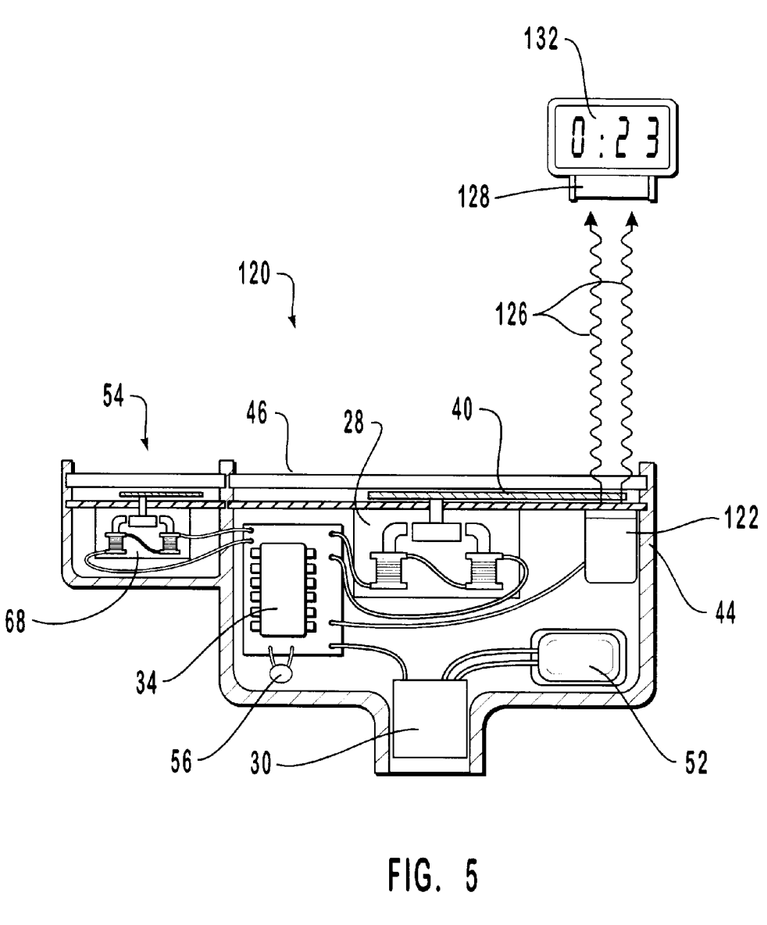
FIG. 5 illustrates another embodiment of a pressure gauge according to the invention, including a timing mechanism and an infrared signal transmission system for displaying inflation history on a remote display unit.

The duration of inflation of a balloon at the tip of a catheter in coronary angioplasty is generally monitored by the operating physician to ensure that heart tissue does not become oxygen-deprived when the inflated balloon blocks a coronary artery. Thus, the duration of inflation is ordinarily monitored in real time during the procedure. Accordingly, pressure gauge 120 of FIG. 5 illustrates an optional embodiment of the invention, which includes timing means for measuring the duration of inflation so that fluid pressure and duration may be displayed on the same device. The timing means may include, for example, a timing mechanism 54, comprising a stepper motor 68, that is activated when the plunger of a syringe is actuated and that is deactivated when the fluid pressure is released. Alternatively, the duration of inflation may be measured and monitored using a timing device that is separate from the pressure gauges of the invention.

It is often important for a physician to be able to retrieve and view a history of past inflation pressures and the duration of past inflations of a balloon tipped catheter. Accordingly, pressure gauge 120 may optionally include digital processor means for electronically recording data relating to the magnitude and/or the duration of the generated fluid pressure. Such digital processor means may be included in microprocessor 34 by providing circuitry or executable code so that microprocessor 34 executes the first step of deriving data from the digital signals, which represent a numerical value of the magnitude of the generated pressure and the duration of inflation of the balloon-tipped catheter and the second step of storing the derived data for later retrieval and output.

Data retrieval means are optionally included in the pressure gauges of the invention to allow a physician or a technician to view the data that has been stored by the digital processor means. The elements of the data retrieval means, at least those that are contained in the sterilizable housing, should be able to withstand sterilization temperatures. One example of the data retrieval means includes a system whereby button 65 of FIG. 2 causes microprocessor 34 to execute a routine whereby the most recent inflation data is recalled and displayed on dial 42 by pointer 40. In this case, button 65 is an example of user input means for actuating a display of pressure history on a visual display device.

An alternative example of the data retrieval means may include an infrared, radio frequency, or another electromagnetic transmission system that allows the inflation history to be displayed on a unit that is physically separated from the sterilizable housing unit. For example, as seen in FIG. 5, the data retrieval means may include an infrared emitter 122 unit that generates electromagnetic signals that correspond to the recorded inflation data. Thus, the infrared emitter 122 is one example of emission means for emitting a series of electromagnetic signals corresponding to the recorded inflation data. "Electromagnetic signals" should be understood to mean signals or information transmitted from a source to a remote destination using electromagnetic radiation that passes through the intervening medium, such as air.

The electromagnetic signals 126 are directed to a receiver unit 128 that is preferably nearby, but physically separated from pressure gauge 120. Receiver unit 128 processes electromagnetic signals 126 to form a visual display 132 of the recorded data according to processes that are understood by one skilled in the art. As such, receiver unit 128 is one example of data display means for detecting the electromagnetic signals and for producing a visual display of the recorded data. A preferred communications protocol for transmitting the pressure data between infrared emitter 122 and receiver unit 128 is InfraRed Data Association (IRDA).

It should also be noted that pressure gauge 120 of FIG. 5 preferably includes at least the elements and features of pressure gauge 10 of FIGS. 1 and 2, with the additional structure and functions disclosed herein.

Furthermore, the pressure gauges may be adapted in other ways to display inflation and pressure history. For example, dial 42 may be equipped with a freely-rotatable pointer (not shown) that is coaxial with pointer 40 and is pushed by pointer 40 as it rotates. As pointer 40 moves to a position on dial 42 so as to indicate a maximum value of fluid pressure, the freely-rotatable pointer is carried by pointer 40 to the same position. The freely-rotatable pointer comes to rest at the maximum pressure position on dial 42 and remains there, even after pointer 40 moves away from the maximum pressure position. In this manner, a physician or technician may easily identify the greatest value of fluid pressure that has been measured.

The present invention preferably includes means for initializing the pressure gauge such that the pressure gauge is initialized or "zeroed" before use. In particular, "zeroing" a pressure gauge generally involves displaying substantially zero units force per unit area prior to each use. It is well understood that a microprocessor used in conjunction with a measurement instrument can set the measurement to zero before each use to ensure that calibration is satisfactory.

Zeroing the pressure gauge is important in some applications, because it is sometimes possible for stepper motor 28 to be inadvertently rotated one or more angular steps from the zero position on graduated dial 42. One example of the initialization means includes a system by which microprocessor 34 causes pointer 40 to rotate until it makes contact with a stop post 67. The stop post 67 is positioned in a known location relative to the "zero" position on graduated dial 42. Microprocessor 34 may thereby determine the relative position of pointer 40 in order to move pointer 40 to the zero position. It is to be understood that the initialization means may be included within microprocessor 34 according to other methods that may be understood by persons skilled in the art.

The pressure gauges of the invention are further preferably capable of adjusting the pressure readings so as to compensate for temperature effects. In mechanical systems, variations in temperatures often cause the displayed pressure to be inaccurate. However, microprocessor 34 and other features of the invention make possible temperature compensation. In particular, the pressure readings may be calibrated for temperature effects by a system that includes temperature sensing means, included in pressure gauge 120 of FIG. 5, for measuring the temperature at which the pressure gauge is operated and for outputting temperature data. The temperature sensing means are integrally included in some preferred microprocessors. Alternatively, the temperature sensing means may include a temperature sensor 56 that is encased in bottom housing 44 and generates an electrical signal that is directed to microprocessor 34.

Temperature adjustment may be further accomplished by adjustment means for receiving the temperature data and for adjusting the digital signals such that the visual display of the magnitude of the generated fluid pressure compensates for temperature effects. One example of such adjustment means includes circuitry and/or executable code within microprocessor 34 that adjusts the digital signals in order to cancel out the temperature distortions that would otherwise exist.

The pressure gauges of the invention may further include warning means for producing an error signal when the measured temperature falls outside a selected acceptable operating temperature range. Such warning means may be provided in addition to, or may take the place of, the foregoing temperature adjustment means. As illustrated in FIG. 3, the warning means may include, for example, software driven digital processing circuitry or hardware based circuit design of microprocessor 34 that activates a warning light 58 that is viewable by a person operating the balloon tipped catheter. Warning light 58 may be a light emitting diode positioned on the face of numerically graduated dial 42. Alternatively, the warning means may produce an error signal by causing pointer 40 to rotate into a position outside the normal operating range of rotation. For example, pointer 40 may rotate beyond the graduated scale on dial 42 to a position on dial 42 reserved for indicating an error condition of the pressure gauge. It will be appreciated that the foregoing error signals may also indicate other conditions in addition to extreme temperatures.

The temperature sensing means may also serve to deactivate the pressure gauge when temperatures commonly produced in sterilization operations are detected. Deactivation of the pressure gauge during sterilization protects the moving parts of the pressure gauge from damage that might otherwise occur at elevated temperatures.

Microprocessor 34 or another suitable component of the pressure gauges 10, 110, and 120 may optionally permit the selection and input of various control parameters such as a maximum positive inflation pressure that is to be applied, a maximum duration for applying positive inflation pressure, initializing the date and time of the procedure and/or retrieving and displaying inflation data previously recorded for any prior inflation of the balloon catheter or other balloon type member. Input of the foregoing parameters may be permitted by button 65 or by any other suitable means. In this manner, the system and method of the present invention provide not only convenient display of the pressure generated during inflation of the balloon catheter, but also a system for alerting a physician or clinician when the appropriate levels of pressure and duration have been reached.

FIG. 3 illustrates the visible portion of the display means under the present invention. The display means preferably includes at least a primary dial 42 across which rotatable pointer 40 moves. In one embodiment of the invention, a secondary dial 60 is provided to increase the resolution and precision at which the pressure is measured and displayed. The secondary dial 60 is in rotational relation to primary dial 42 such that rotation of primary pointer 40 is accompanied by simultaneous rotation of secondary pointer 62. In particular, rotation of primary pointer 40 through a first angle 64 is accompanied by rotation of secondary pointer 62 through a second angle 66 that is greater than the first angle. Thus, secondary dial 60 displays measurement increments that are smaller than those of primary dial 42. Secondary pointer 62 may be driven by any of a number of suitable means, including a separate stepper motor or by being configured in a geared relationship with the stepper motor that drives primary pointer 40.

The positioning of secondary dial 60, if used, may be different from that depicted in FIG. 3. For example, primary pointer 40 and secondary pointer 62 may be coaxial and move across a common dial. In this case, the common dial may have multiple graduated scales inscribed thereon, with one graduated scale being associated with each of the coaxial pointers.

Optionally, the pressure gauge of the invention may employ a system by which one pointer 40 is used to display pressure information on dial 42 in multiple units or according to varying orders of magnitude. For example, a user may select the measurement units to be used by depressing button 65, which causes microprocessor 34 to change the units of measurement.

There may also be an illumination system for backlighting the dials 42 and/or 60 to increase the visibility thereof. As illustrated in FIG. 2, the illumination system may comprise an electroluminescent lighting unit 63 of the type that is commonly used to illuminate timepieces. The illumination system may be controlled and activated by microprocessor 34 or may be manually actuated.

Under normal operating conditions, the pressure gauges disclosed herein can be expected to have a usable lifespan of at least 5 to 6 years. In general, the limiting factor is the duration of the preferred lithium battery. Moreover, the absence of especially delicate components in the pressure gauges of the invention significantly reduce the likelihood that the gauges will fail due to rough operating conditions or mishandling. The relatively long lifespan and the durability of the pressure gauges provide significant advantages compared to many other pressure gauges.

The pressure gauges of the invention are also very useful in industrial settings in which measuring instruments must be exposed to high temperatures, rough handling, or vibration. For example, when such conditions are expected, the ability to display the magnitude of fluid pressure without using liquid crystal displays is advantageous, particularly if high temperatures above about 60° C. are to be experienced.

Another advantage of the electronic pressure gauges in industrial settings is that the microprocessor may be programmed to damp out frequent pressure fluctuations to allow the gauge to have a long usable life or to make the gauge easier to read. The microprocessor may be adapted as desired in order to process pressure measurements obtained from a cyclical or variable pressure system. For example, the pressure gauge may only display the maximum pressure value, the minimum pressure value, the average or median pressure of such a cyclical system, or any other selected set of measurements.

A presently preferred method of monitoring and displaying fluid pressure generated within a syringe using a pressure gauge of the invention is described below. First, a balloon-tipped catheter is introduced into the vascular system of a patient and the catheter is connected to a syringe. A pressure gauge such as those disclosed herein is removably positioned on the syringe and is placed in fluid communication therewith. The physician manipulates the handle of the syringe and actuates the plunger, thereby expelling fluid from the barrel of the syringe and generating fluid pressure within the barrel. The semiconductor transducer of the pressure gauge senses the generated fluid pressure and outputs an electrical signal that changes in response to changes in the fluid pressure.

The electrical signal is directed to a microprocessor or another conversion module which converts the electrical signal into corresponding digital signals. The digital signals are transmitted to a display device that utilizes a stepper motor in order to mechanically produce a visual display that represents the magnitude of the fluid pressure. The operating physician or an assistant monitors the display and adjusts the manipulation of the plunger so as to achieve the desired magnitude of generated fluid pressure. After the pressure is applied for the desired duration, the syringe is deactivated, thereby removing the fluid pressure.

The foregoing series of steps relating to generating and monitoring fluid pressure may be repeated as needed. After inflation of a balloon is conducted the desired number of times and the medical procedure is completed, the pressure gauge is removed from the syringe. A sterilization process may be conducted in an autoclave or using a sterilizing chemistry, among other alternatives. After the pressure gauge is adequately sterilized, the pressure gauge may be reattached to the syringe for reuse.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A syringe system for inflating a balloon-tipped catheter comprising:
   a syringe comprising a barrel and a plunger selectively operable to increase or decrease fluid pressures by inserting the plunger into the barrel to expel fluid into the catheter or by retracting the plunger to permit reentry of fluid into the barrel from the catheter, respectively;
   a housing well defining a port on the barrel of the syringe; and
   a removable pressure gauge comprising:
      a housing which includes a neck portion that removably mates with said housing well of the syringe, the neck portion holding a transducer with a diaphragm disposed across the neck portion and which encloses the bottom of the housing while permitting fluid within the syringe barrel to be communicated through said port to the diaphragm disposed within said neck portion to detect pressures of the fluid within the syringe barrel, the housing further including a transparent window which encloses the top of the housing; and
   wherein the housing contains within it:
      a graduated dial that represents in discrete increments a plurality of pressures and a pointer for indicating pressure by pointing to a particular one of the increments;
      a stepper motor connected to the pointer and which drives the pointer in discrete increments corresponding to the increments on the dial;
      a microprocessor connected to the transducer and programmed so that pressures detected by the transducer are converted to digital signals used to control movement of the pointer by means of the stepper motor; and
      a battery connected to the transducer, microprocessor and the stepper motor to supply electrical energy to each.

2. The syringe system as defined in claim 1 wherein said microprocessor is programmed to perform at least one of the following functions:
   detecting from said transducer the magnitude and duration of each inflation of the balloon;
   detecting from said transducer the duration of each deflation of the balloon;
   recording and digitally storing data that represents the magnitude and duration of each inflation of the balloon; and
   recording and digitally storing data that represents the duration of each deflation of the balloon.

3. The syringe system as defined in claims 1 or 2 wherein said transducer is sized so that it is removably received by the neck portion of said housing so that not only is the housing removeable from the syringe barrel, but the transducer is also removeable from the housing.

4. The syringe system as defined in claims 1 or 2 wherein said housing contains a second stepper motor and a timing mechanism driven by said second stepper motor, said timing mechanism providing a visual indication of the duration of a particular inflation or deflation event.

5. The syringe system as defined in claim 2 further comprising a manually operable switch on said housing that activates said microprocessor to retrieve for display purposes of said at least one or more functions.

6. The syringe system as defined in claim 5 wherein said housing contains an emitter for transmitting electromagnetic signals to a remote display unit for display purposes of said at least one or more functions, and a second manually operable switch on said housing that activates said emitter.

7. The syringe system as defined in claims 1 or 2 wherein said graduated dial is a main dial, and further comprising a second a graduated dial with a pointer that indicates in discrete increments a plurality of pressure gradations, the gradations of the secondary dial corresponding to gradations between each of the gradations on the main dial, and a pointer for indicating pressure by pointing to a particular one of the increments on the second dial to permit a more fine determination of the applied pressure, and said second dial connected to said stepper motor to drive the pointer thereof in discrete increments corresponding to the increments on the second dial.

8. An improved syringe system for inflating a balloon-tipped catheter, the system including a syringe comprising a barrel and a plunger selectively operable to increase or decrease fluid pressures by inserting the plunger into the barrel to expel fluid into the catheter or by retracting the plunger to permit reentry of fluid into the barrel from the catheter, respectively, and a housing well defining a port on the barrel of the syringe, and wherein the improvement comprises:

a removable pressure gauge comprising:

a housing which includes a neck portion that removably mates with said housing well of the wyringe, the neck portion holding a transducer with a diaphragm disposed across the neck portion and which encloses the bottom of the housing while permitting fluid within the syringe barrel to be communicated through said port to the diaphragm disposed within said neck portion to detect pressures of the fluid within the syringe barrel, the housing further including a transparent window which encloses the top of the housing; and wherein the housing contains within it:

a graduated dial that represents in discrete increments a plurality of pressures and a pointer for indicating pressure by pointing to a particular one of the increments;

a stepper motor connected to the pointer and which drives the pointer in discrete increments corresponding to the increments on the dial;

a microprocessor connected to the transducer and programmed so that pressures detected by the transducer are converted to digital signals used to control movement of the pointer by means of the stepper motor; and a battery connected to the transducer, microprocessor and the stepper motor to supply electrical energy to each.

9. The syringe system as defined in claim 8 wherein said microprocessor is programmed to perform at least one of the following functions:

detecting from said transducer the magnitude and duration of each inflation of the balloon;

detecting from said transducer the duration of each deflation of the balloon;

recording and digitally storing data that represents the magnitude and duration of each inflation of the balloon; and recording and digitally storing data that represents the duration of each deflation of the balloon.

10. The syringe system as defined in claims 8 or 9 wherein said transducer is sized so that it is removably received by the neck portion of said housing so that not only is the housing removeable from the syringe barrel, but the transducer is also removeable from the housing.

11. The syringe system as defined in claims 8 or 9 wherein said housing contains a second stepper motor and a timing mechanism driven by said second stepper motor, said timing mechanism providing a visual indication of the duration of a particular inflation or deflation event.

12. The syringe system as defined in claim 9 further comprising a manually operable switch on said housing that activates said microprocessor to retrieve for display purposes of said at least one or more functions.

13. The syringe system as defined in claim 12 wherein said housing contains an emitter for transmitting electromagnetic signals to a remote display unit for display purposes of said at least one or more functions, and a second manually operable switch on said housing that activates said emitter.

14. The syringe system as defined in claims 8 or 9 wherein said graduated dial is a main dial, and further comprising a second a graduated dial with a pointer that indicates in discrete increments a plurality of pressure gradations, the gradations of the secondary dial corresponding to gradations between each of the gradations on the main dial, and a pointer for indicating pressure by pointing to a particular one of the increments on the second dial to permit a more fine determination of the applied pressure, and said second dial connected to said stepper motor to drive the pointer thereof in discrete increments corresponding to the increments on the second dial.

15. An improved syringe system for inflating a balloon-tipped catheter, the system including a syringe comprising a barrel and a plunger selectively operable to increase or decrease fluid pressures by inserting the plunger into the barrel to expel fluid into the catheter or by retracting the plunger to permit reentry of fluid into the barrel from the catheter, respectively, and a housing well defining a port on the barrel of the syringe, and wherein the improvement comprises:

a removable pressure gauge comprising:

a means for encasing components of the pressure gauge, and comprising means for removable attachment of the encasing means with said housing well of the syringe, and said encasing means comprising a transparent top portion to permit viewing pressure indications; and wherein the means for encasing contains within it:

a transducer with a diaphragm disposed within the means for removable attachment so as to enclose the removable attachment means while permitting fluid within the syringe barrel to be communicated the diaphragm to detect pressures of the fluid within the syringe barrel;

a display means for mechanically producing a visual display, in discrete increments, of the magnitude of the fluid pressure being exerted by means of the syringe, and detected by the transducer, said display means including a stepper motor for mechanically driving the display means;

a microprocessor connected to the transducer and programmed so that pressures detected by the transducer are converted to digital signals used to control movement of the pointer by means of the stepper motor; and a battery connected to the transducer, microprocessor and the stepper motor to supply electrical energy to each.

* * * * *

UNITED STATES PATENT AND TRADEMARK OFFICE
CERTIFICATE OF CORRECTION

PATENT NO. : 6,394,977 B1
DATED : May 28, 2002
INVENTOR(S) : Steven R. Taylor and Thomas D. Stout It is certified that error appears in the above-identified patent and that said Letters Patent is hereby corrected as shown below:

Title page,
Item [57], ABSTRACT,
Line 8, before "to digital signals" replace "converts d" with -- converted --

Column 2,
Line 26, after "from the syringe to" delete "a"

Column 6,
Line 31, after "are" replace "use(in" with -- used in --

Column 17,
Line 10, after "housing well of the" replace "wyringe" with -- syringe --

Signed and Sealed this

Fourth Day of March, 2003

JAMES E. ROGAN
*Director of the United States Patent and Trademark Office*